United States Patent [19]

Wolf et al.

[11] Patent Number: 4,497,334
[45] Date of Patent: Feb. 5, 1985

[54] CLEANING APPARATUS FOR LIQUID DELIVERY SYSTEMS

[76] Inventors: Leo H. Wolf, Rte. 5, Box 363, River Falls, Wis. 54022; Hugo M. Wolf, 1451 NE. Glacier La., Minneapolis, Minn. 55421

[21] Appl. No.: 397,454

[22] Filed: Jul. 12, 1982

[51] Int. Cl.³ .............................................. B67D 5/54
[52] U.S. Cl. ..................................... 137/209; 137/240; 137/625.68; 220/315; 222/148; 222/400.7
[58] Field of Search ...................... 137/240, 209, 625.4, 137/625.48, 625.68; 251/325; 220/315, 324; 222/148, 400.7, 136, 145

[56] References Cited

U.S. PATENT DOCUMENTS

| | | | |
|---|---|---|---|
| 193,321 | 7/1877 | Coffin | 220/324 |
| 389,652 | 10/1888 | Heltzle | 137/625.68 X |
| 565,600 | 8/1896 | Braun | |
| 844,332 | 2/1907 | Demacakos | 251/325 X |
| 1,114,358 | 10/1914 | Hooker | 222/148 |
| 1,572,727 | 2/1926 | Kerr | 222/400.7 |
| 2,066,397 | 1/1937 | Fogarty | 222/136 X |
| 2,591,985 | 4/1952 | Warcup | 225/12 |
| 2,606,736 | 8/1952 | Ferm | 137/625.68 |
| 2,619,119 | 11/1952 | Warcup | 137/652 |
| 2,903,151 | 10/1959 | Alcaro | 220/324 X |
| 2,981,660 | 4/1961 | Achorn, Jr. et al. | 195/142 |
| 3,044,466 | 7/1962 | Henderson | 128/276 |
| 3,044,483 | 7/1962 | Wilburn | 137/239 |
| 3,169,545 | 2/1965 | Kolling | 137/209 |
| 3,420,399 | 1/1969 | Heisler | 220/324 |
| 3,613,723 | 10/1971 | Witt | 137/604 |
| 4,061,504 | 12/1977 | Zall et al. | 134/95 |

FOREIGN PATENT DOCUMENTS 41367  5/1967  German Democratic Rep. ................................. 137/209

*Primary Examiner*—Martin P. Schwadron
*Assistant Examiner*—Stephen M. Hepperle
*Attorney, Agent, or Firm*—Burd, Bartz & Gutenkauf

[57] ABSTRACT

Apparatus for cleaning a liquid delivery system, comprising a container having an open top, a control housing removably closing the top of the container and having a supply conduit extending to the bottom of the container, an inlet connection for connecting the housing to a source of air under pressure, an outlet connection for connecting the housing to a liquid delivery system, and valving mechanism in the housing, including first and second valves actuable between normal positions and operated positions, and a conduit interconnecting the valves, the first valve having a normally closed position and an operated position in which the source is connected to the conduit inter-connecting the valves, and the second valve having a normal position in which the inter-connecting conduit is connected to the outlet connection, and an operated position, in which the supply conduit is connected to the outlet connection.

25 Claims, 5 Drawing Figures

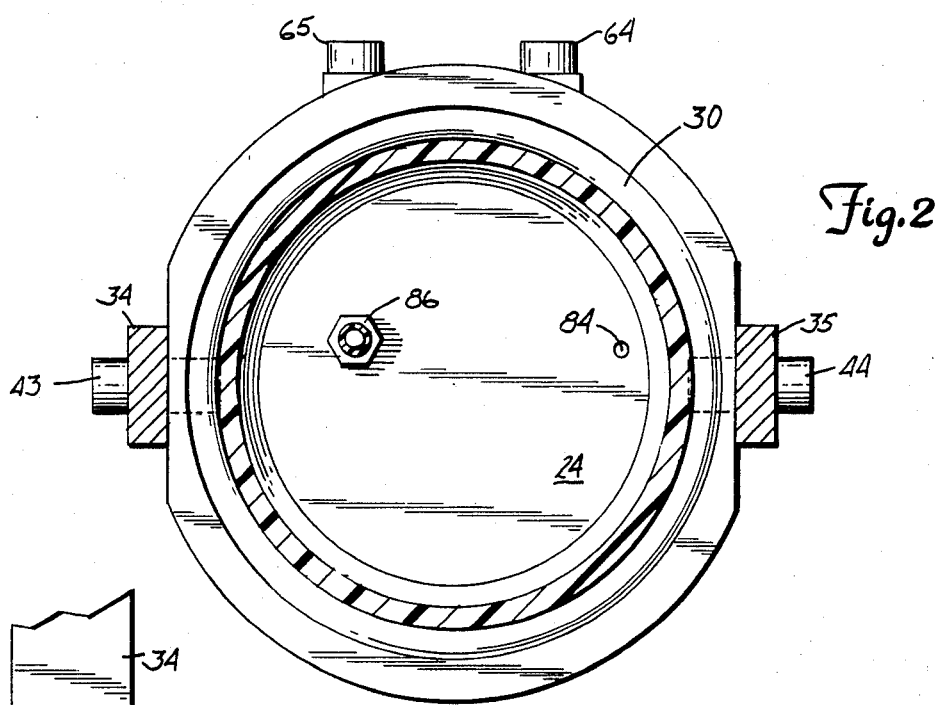
Fig.2
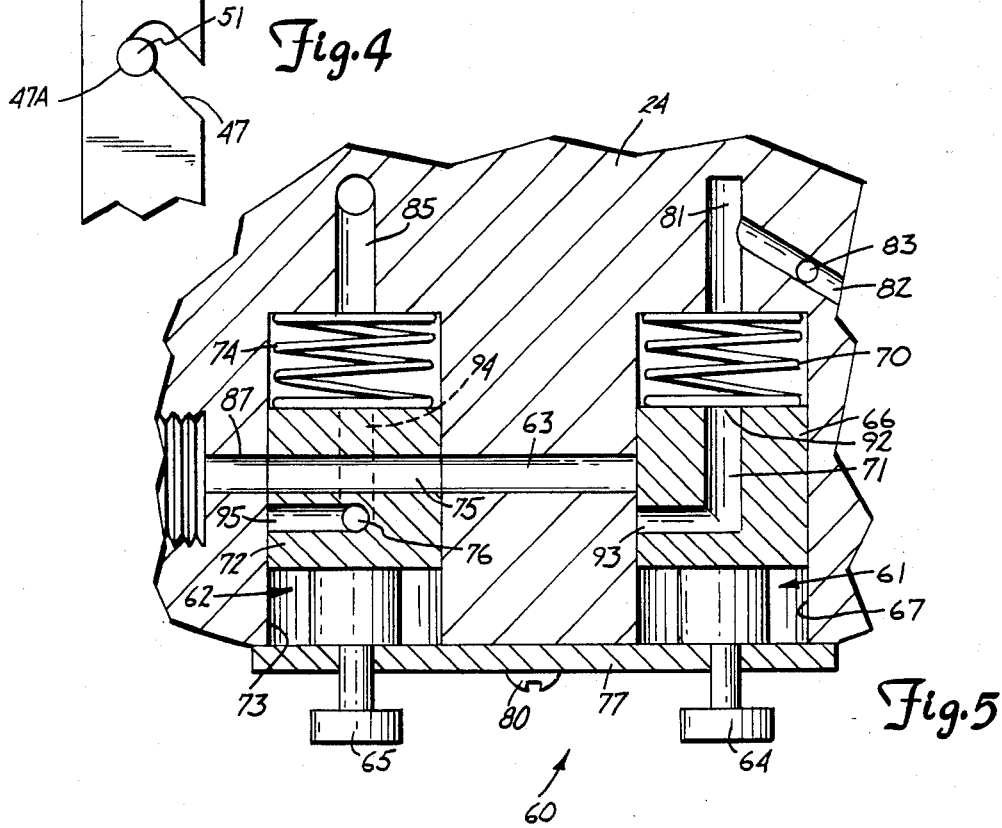
Fig.4
Fig.5

CLEANING APPARATUS FOR LIQUID DELIVERY SYSTEMS

TECHNICAL FIELD

This invention relates to the field of dentistry, and specifically to an apparatus and a method for cleaning water delivery systems in dental offices.

BACKGROUND OF INVENTION

A feature common to dental treatment equipment is a water delivery system including a flexible conduit connected between the main water supply and a hand piece including a nozzle and a manual and/or automatic control operable to cause discharge of water from the nozzle to rinse the area of the patient's mouth upon which work is being done. The water is discharged only intermittently as needed, and water stands in the system for considerable intervals.

It has been found that such systems often become contaminated, whether by micro-organisms carried in the water and attached to the conduits, or by organisms finding their way into the nozzle from the patient's mouth. It is desirable to clean such micro-organisms and other undesirable material from the system, so that it will be decontaminated and sanitary.

BRIEF DESCRIPTION OF THE INVENTION

The present invention comprises an apparatus and a method for periodically cleaning and decontaminating such water delivery systems, the apparatus to remain permanently associated with the system, and to use a compressed air source generally present in dental equipment to first flush out standing water, then replace it for a cleaning interval with a decontaminating liquid, and finally flushing that liquid from the system to prepare it for normal water delivery.

Various advantages and features of novelty which characterize the invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there is illustrated and described a preferred embodiment of the invention.

BRIEF DESCRIPTION OF THE DRAWING

In the drawing, in which like reference numerals identify corresponding parts throughout the several views, FIG. 2 is a bottom view of a housing shown in FIG. 1.

DESCRIPTION OF PREFERRED EMBODIMENT

Figure 1:
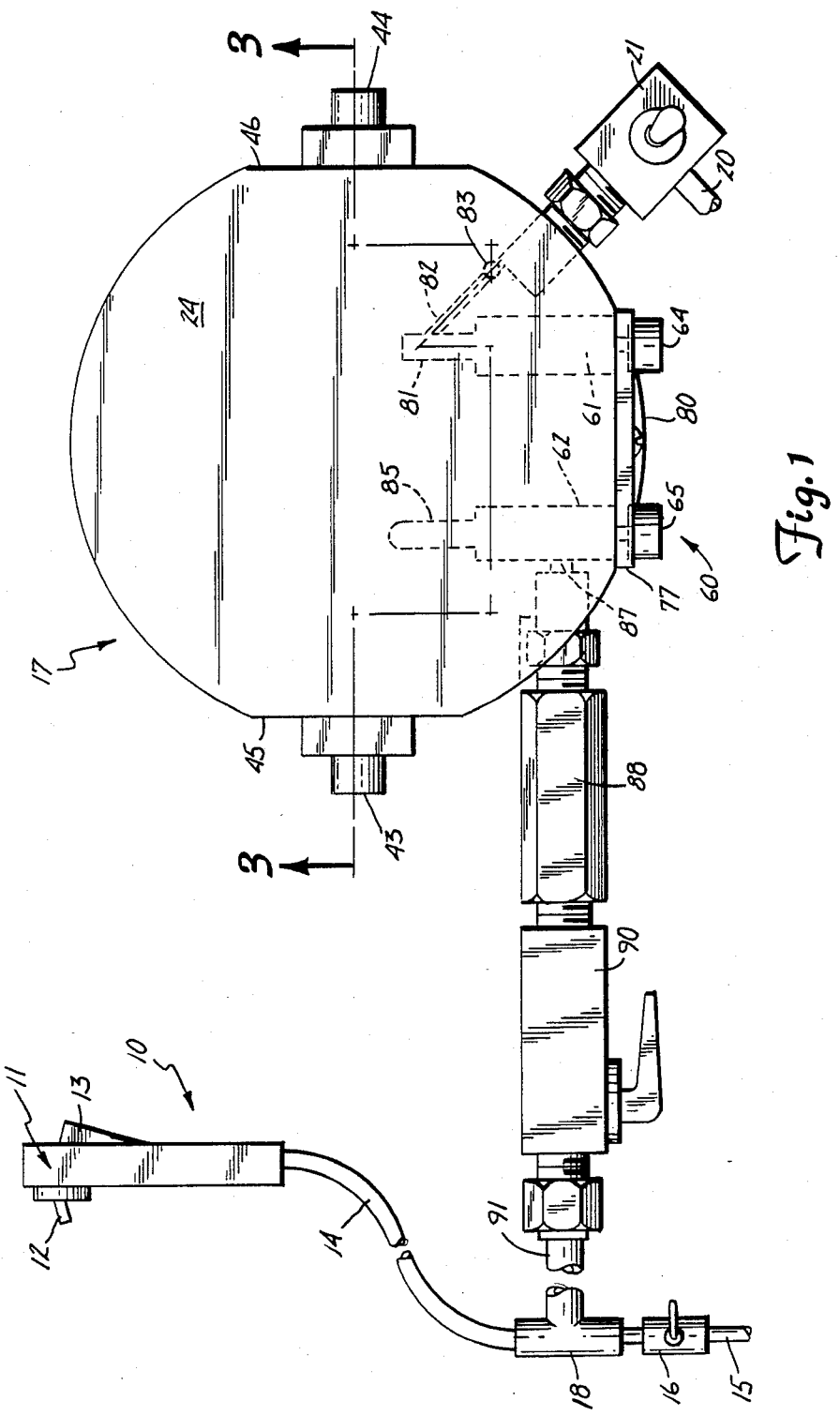
FIG. 1 is a plan view of the apparatus according to the invention, showing it applied to a water delivery system.
Figure 3:
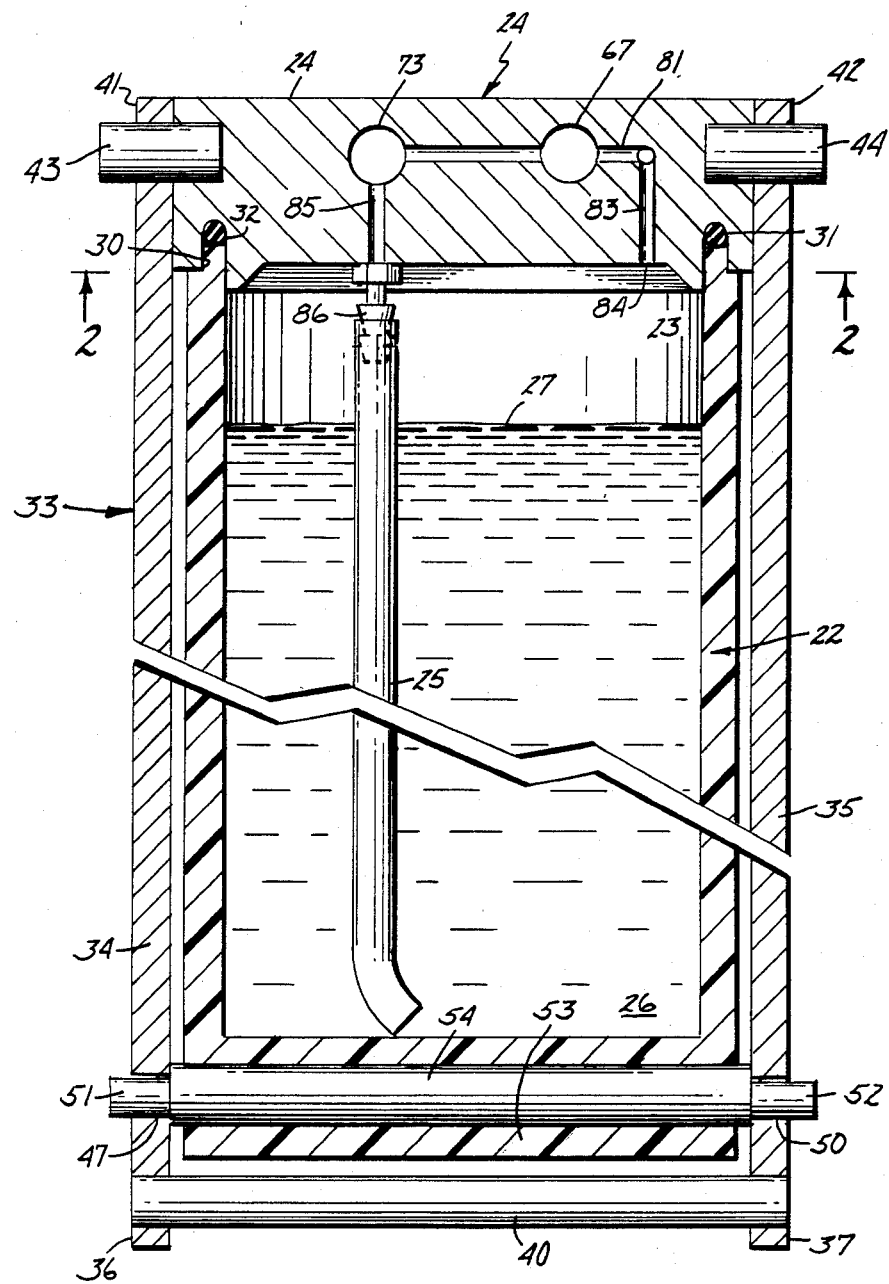
FIG. 3 is a sectional view taken generally along the line 3—3 of FIG. 1, and FIGS. 4 and 5 are fragmentary detailed views, the latter showing a valving means contained in a housing according to the invention.

Referring to FIG. 1, a liquid delivery system 10 common in dental offices is shown to comprise an instrument 11 having a nozzle 12 and a manual control 13 by which water is released through nozzle 12 from a flexible conduit 14 connected to a source 15 under the control of a valve 16 which is normally open during working hours. The cleaning apparatus 17 of the present invention is connected to system 10 at a T-connection 18, and is supplied with air under pressure, from the usual source through a conduit 20, under the control of a valve 21, which is normally closed.

The equipment comprises a container 22 having an open top 23 closed by a cover or control housing 24 from which it is removable, and a flexible supply conduit 25 extending from housing 24 to open at the bottom of the chamber 26 of the container, to receive the cleaning liquid 27 contained therein.

Housing 24 has an annular groove 30 containing an O-ring 31 to sealingly engage a lip 32 at the top or rim of container 22. The container and housing are maintained in sealed relationship by a quick release structure 33 including a pair of arms 34 and 35 extending downwardly from housing 24, inter-connected at their lower ends 36 and 37 by a cross member 40, and pivoted near their upper ends 41 and 42 to pivots 43 and 44 extending coaxially outward in opposite directions from housing 24, which is flattened at sides 45 and 46 to enable the pivotal movement. Arms 34 and 35 are provided near their lower ends with slots 47 and 50, which receive a pair of studs 51 and 52 projecting coaxially outward in opposite directions from the bottom 53 of the container. If desired, studs 51 and 52 can be the ends of rod 54 passing through or embedded in the bottom of container 22. As suggested in FIG. 4, slots 47 and 50 can be of sloping "bayonet" or reverse curve configuration to assist in completing and maintaining the sealed relation between housing 24 and container 22 at O-ring 31. Slot 47 has a seat 47A which releasably accommodates the stud 51. In assembly of container 22 to housing 24, lip 32 is inserted in groove 30 in bearing relationship to O-ring 31 with arms 36, 37 pivoted to an out of the way location. Arms 36, 37 are then pivoted to position cross member 40 beneath container 22. Studs 51, 52 ride up slots 47, 50 against the influence of O-ring 31, then drop into the respective seats of the slots. The opposite procedure is followed in disassembly of container 22 from housing 24. In assembled configuration, lip 32 is held in compressing relationship to O-ring 31 by studs 51,52.

Housing 24 includes valving means 60 suggested in broken lines in the top view of FIG. 1, and shown more clearly in fragmentary section to a larger scale in FIG. 5. It includes a first valve 61 and a second valve 62 inter-connected by a conduit 63, the valves having normal positions out of which they can be individually actuated by push button actuators 64 and 65 accessible from outside the housing.

Valve 61 comprises a spool 66 movable by actuator button 64 in a chamber 67 in housing 24 against the force of a compression spring 70, and having a right angle bore 71. Valve 62 comprises a spool 72, movable by actuator 65 in a second chamber 73 in housing 24 against the force of a compression spring 74. Valve 62 has a cross bore 75 and an angle bore 76. Movement of spools 66 and 72 by actuators 64 and 65 is limited by a mounting plate 77 secured to housing 24 as by a fastener 80.

Chamber 67 is connected by conduits 81 and 82 with air inlet valve 21, and a branch conduit 83 leads from conduit 82 to an opening 84 located at the bottom of housing 24 radially inward of groove 30 and open to the top of container 22.

Chamber 73 is connected by a conduit 85 and a hose connection 86 to flexible conduit 25. Chamber 73 is also connected by a conduit 87, a check valve 88, a manual valve 90, and a conduit 91 to T-connection 18.

A first end 92 of bore 71 of first valve 61 is continuously in communication with conduit 81. In the normal position of valve 61 the second end 93 of bore 71 is closed by the wall of chamber 67. When actuator 64 operates the valve, spool 66 moves so that end 93 of bore 71 is in alignment with conduit 63.

A first end 94 of bore 76 of valve 62 is in continuous communication with conduit 85. In the normal position of second valve 62 the second end 95 of bore 76 is closed by the wall of chamber 73. When actuator 65 operates the valve, spool 72 moves so that end 95 of bore 76 is in alignment with conduit 87. Also, in the normal position of spool 72, cross bore 75 connects conduits 63 and 87, while in the operated position of the valve this connection is interrupted at both ends by the walls of chamber 73.

OPERATION

In normal operation of the liquid delivery system valve 16 is open to provide water to instrument 11, backflow of water into housing 24 being prevented by check valve 88. Valve 90 may also be closed, if desired. Valve 21 is also closed, to cut off air supply from conduit 20. When it is desired to clean the liquid delivery system 10, container 22 is removed from housing 24 by displacement of release structure 33, filled with cleaning liquid 27, and repositioned beneath housing 24. The volume of chamber 26 is greater than the volume of system 10 from T-connection 18 to nozzle 12.

The cleaning is to be performed overnight or on a weekend. To accomplish it, valve 16 is closed, valve 90 if closed is opened, and valve 21 is opened. Compressed air may now pass from valve 21 through conduits 82 and 83 to the top of container 22, but the container is closed and no result follows at this time.

The next step is opening valve 61, by pressing actuator 64, and operating instrument control 13. The air may now pass from valve 21 through conduits 82 and 81, chamber 67, angle bore 71, conduit 63, cross bore 75, conduit 87, valves 88 and 90, conduit 91, T-connection 18, conduit 14, and instrument 11 to nozzle 12, flushing before it the water remaining in delivery system 10.

When air free from water emerges from nozzle 12, actuator 64 is released and actuator 65 is operated. The air pressure above the liquid 27 in container 22 forces the liquid out conduit 25, through hose connection 86, conduit 85, angle bore 76, conduit 87, valves 88 and 90, conduit 91, T-connection 17, conduit 14, and instrument 11 to nozzle 12. When liquid begins to discharge from nozzle 12, the delivery system is charged with cleaning fluid, and actuator 65 and instrument control 13 are released. Valves 90 and 21 may now be closed, and the cleaning process accomplished by liquid 27 is allowed to proceed for a desired interval.

At the beginning of the next work period valves 21 and 90 are opened, actuator 64 and instrument control 13 are operated, and air pressure flushes the cleaning fluid out of the system through nozzle 12. When air free from liquid emerges at the nozzle, actuator 64 is released, valves 90 and 21 are closed, and valve 16 is opened to admit water to the system. After a steady flow of clear water is obtained at nozzle 12, instrument control 13 is released, and the system is ready for use.

From the above, it will be evident that the invention comprises a method and apparatus for cleaning dental water delivery systems, using compressed air to flush standing water from the system, replace it for a cleaning interval with a cleaning liquid, and then flush the cleaning liquid from the system.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning if the terms in which the appended claims are expressed.

The embodiments of the invention in which an exclusive property or privilege is claimed are defined as follows:

1. Cleaning apparatus for a liquid delivery system comprising:
    a container having an open top;
    a control housing removably closing the top of said container, and having a supply conduit extending to the bottom of said container;
    inlet means for connecting said housing to a source of air under pressure;
    outlet means for connecting said housing to a liquid delivery system;
    valving means in said housing, including first and second valves, actuable between normal positions and operated positions, conduit means interconnecting said valves, and means external to said housing for manually actuating each of said valves into the operated position thereof:
    said first valve having a normally closed position and an operated position, in which said source is connected to said conduit means;
    and said second valve having a normal position, in which said conduit means is connected to said outlet means and an operated position, in which said supply conduit is connected to said outlet means and an operated position, in which said supply conduit is connected to said outlet means;
    so that operation of only said first valve connects air from said source to said delivery system through said second valve to enable liquid to be flushed therefrom, and so that operation of only said second valve enables fluid in said container to be supplied to said delivery system by pressure of the air from said source; and
    quick release structure for removably interconnecting said housing and said container, said structure comprising a pair of arms pivotal about a central axis to said housing, a pair of struts projecting oppositely from the sides of said container at the bottom thereof, and means carried by said arms for engaging said struts to support said container against said housing.

2. Cleaning apparatus according to claim 1 further including means preventing flow of liquid from said delivery system to said container.

3. Cleaning apparatus according to claim 1 in which said valving means normally prevents flow of liquid from said delivery system to said container.

4. Cleaning apparatus according to claim 1 in which said first valve comprises a spool movable in a chamber and having an angle bore, one end of which is permanently in communication with said inlet means and the other end of which is actuable into communication with said conduit means.

5. Cleaning apparatus according to claim 1 in which said second valve comprises a spool movable in a chamber and having a cross bore which normally connects said conduit means with said outlet means.

6. Cleaning apparatus according to claim 1 in which said second valve comprises a spool movable in a chamber and having an angle bore, one end of which is permanently connected to said supply conduit, and the other end of which is actuable into communication with said outlet means.

7. Cleaning apparatus according to claim 1 in which said second valve comprises a spool movable in a chamber and having a cross bore which normally connects said conduit means with said outlet means, and an angle bore, one end of which is permanently connected to said supply conduit, and the other end of which is actuable into communication with said outlet means.

8. An apparatus for selectively dispensing a first or a second fluid through a common outlet, comprising:
a housing having a first valve means connectable to a first fluid supply and a second valve means connectable to a second fluid supply;
a fluid outlet from the housing;
said first valve means having a first valve chamber and a first valving element movably located in the chamber, said first valve chamber being continuously connectable to the first fluid supply;
said second valve means having a second valve chamber and a second valving element movably located in the chamber, said second valve chamber being continuously connectable to the second fluid supply;
fluid conduit means connecting the first valve chamber to the second valve chamber and the second valve chamber to the fluid outlet;
said first valving element normally in a first position in blocking relationship to the fluid conduit means and having a first passage, said first valving element movably to operative position with the first passage located to permit first fluid to move from the first valving chamber to the fluid conduit means and out of the fluid outlet;
said second valving element having a portion of the fluid conduit means and normally in a first position with said portion of the fluid conduit means open to the fluid outlet, to allow the first fluid to flow through the fluid conduit means when the first valve element is in the operative position, said second valve means having a second passage and being movable to an operative position of blocking relationship to the fluid conduit means with the second passage open to the second chamber and the fluid outlet to allow movement of the second fluid from the second valving chamber out of the fluid outlet and prevent flow of the first fluid in the fluid conduit means; and quick release structure for removably interconnecting said housing and said container, said structure comprising a pair of arms pivotally mounted on the housing, a pair of struts projecting oppositely from the sides of said container at the bottom portion thereof, and means carried by said arms for engaging said struts to support said container against said housing.

9. The apparatus of claim 8 including: bias means biasing each of the valving elements in the first position and means external to the housing for manually actuating each of the valving elements into the operative position.

10. The apparatus of claim 9 wherein: said first valving element comprises a spool movable in the first valve chamber and having a bore comprising said first passage, one end of the bore being continuously in communication with first fluid inlet means communicating with the first valving chamber.

11. The apparatus of claim 10 wherein: said second valving element comprises a second spool movable in the second valve chamber and having a cross bore comprising a part of said fluid conduit means, another part of said fluid conduit means being comprised as a bore connecting the first valving chamber and the second valving chamber.

12. The apparatus of claim 11 wherein: said second valve spool has a bore comprising said second passage, one end of said bore being continuously connected to a second fluid inlet means.

13. The apparatus of claim 12 including: actuating means comprised as a first push button connected to the first spool in the first valve chamber and extending externally of the housing for movement of the first spool from the first position to the operative position, and actuating means comprised as a second push button connected to the second valve spool in the second valve chamber and extending externally of the housing for actuating the second spool to move it from the first position to the operative position.

14. The apparatus of claim 13 including: a first helical compression spring located in the first valve chamber positioned to bias the first spool in the closed position, and a second helical compression spring located in the second valve chamber positioned to bias the second spool in the closed position.

15. The apparatus of claim 14 including: a liquid container for holding a liquid comprised as said second fluid and means continuously connecting the interior of the liquid container with the second valve chamber.

16. The apparatus of claim 15 wherein: said housing closes said container, said first fluid being comprised as a gas, means for continuously connecting a gas supply to the first valve chamber, and a fluid passage from the first valve chamber to said container for supplying gas under pressure to said container for movement of the second fluid through the second valve chamber.

17. A cleaning apparatus for cleaning a liquid delivery system with a liquid disinfectant comprising:
a container having an open top for containing a liquid disinfectant;
a housing sealably closing the top of the container;
said housing having a fluid outlet for connection to the fluid delivery system;
said housing having a first valve with a valve chamber connectable to a supply of air under pressure and conduit means connected to the fluid outlet, a first valve element located in the valve chamber in a first position blocking communication between the air supply and the conduit means and movable to a operative position to permit air flow through the conduit means to the fluid outlet;
said housing having a second valve with a second valve chamber connected to the inside of said container and conduit means connected to the fluid outlet, and a second valve element located in the second valve chamber normally in a first position to block liquid disinfectant communication between the container and the conduit means and movable to an operative position to permit flow of liquid disinfectant through conduit means to the fluid outlet whereby sequentially air, liquid disinfectant, and air can be delivered to the liquid delivery system to clean it, and arm means pivotally connected to the housing adapted to straddle the container when the container is assembled to the housing, arm means comprising a pair of arms pivotally connected on opposite sides of the cover and pivotally movable into and out of straddling relationship to the container, a cross member connecting the lower ends of the arm, said container having a pair of oppositely positioned outwardly extended lugs, each of said arms having a reverse turn groove for releasably accommodating one of the lugs to hold the container in sealed engagement with the housing.

18. The cleaning apparatus of claim 17 including: an air supply conduit disposed between the air supply and the top of the container to pressurize the container to move liquid disinfectant through the second valve and the fluid outlet.

19. The cleaning apparatus of claim 18 including: means external to said housing for manually moving the first and second valve elements from the normally closed position into the operative position.

20. The cleaning apparatus of claim 19 including: means preventing flow of fluid from said delivery system to the housing.

21. The apparatus of claim 17 wherein: said housing has a groove having the configuration of the lip whereby the lip seats in the groove when the housing and container are in assembled relationship.

22. The apparatus of claim 21 including: a resilient O-ring located in the groove.

23. A cleaning apparatus for a liquid delivery system comprising: a container for storing a cleaning liquid, said container having an open top, a housing removably closing the top of said container, a fluid supply conduit extended from the housing toward the bottom of said container into the cleaning liquid stored therein, inlet means for connecting said housing to a source of gas under pressure, outlet means for connecting said housing to a liquid delivery system, a first valve actionable between a first position and an operating position, a second valve actionable between a first position and a operated position, conduit means interconnecting said first and second valves, said first valve when in the first position blocking the flow of gas under pressure to the conduit means and when moved to the operated position connecting the source of gas under pressure to the conduit means, said second valve when in the first position connecting the conduit means to said outlet means whereby when said first valve is moved to the operated position the gas flows through the conduit means to the outlet means to delivery gas under pressure to the liquid delivery system, said second valve when in the operated position blocking said conduit means and allowing said cleaning liquid to flow from said container to the outlet means whereby only cleaning fluid is supplied to the liquid delivery system, and quick release structure for removably mounting said container on said housing, said structure including arm means pivotally mounted on said housing, strut means extended from said container adjacent the bottom thereof, and means carried by the arm means for engaging said strut means to support said container on said housing.

24. The apparatus of claim 23 including: valve means connected to the outlet means to prevent the flow of liquid from said liquid delivery system to said container.

25. The apparatus of claim 23 wherein: said first valve and second valve each comprises a spool movable in a chamber in the housing, biasing means engageable with the spool to bias the spool to the first position, and means external to said housing for manually moving the spool to the operated position thereof.

* * * * *